United States Patent
Babu et al.

(10) Patent No.: US 10,940,240 B2
(45) Date of Patent: Mar. 9, 2021

(54) CATHETER LOCKING SOLUTION AND CATHETER LOCKING THERAPY

(71) Applicant: Medical Components, Inc., Harleysville, PA (US)

(72) Inventors: Premkumar Babu, Lansdale, PA (US); Benjamin R. Brozanski, Philadelphia, PA (US); Lisa Pagano, Pottstown, PA (US); Jeffrey S. Bennett, Pottstown, PA (US)

(73) Assignee: Medical Components, Inc., Harleysville, PA (US)

( * ) Notice: Subject to any disclaimer, the term of this patent is extended or adjusted under 35 U.S.C. 154(b) by 238 days.

(21) Appl. No.: 15/425,436

(22) Filed: Feb. 6, 2017

(65) Prior Publication Data

US 2017/0232153 A1    Aug. 17, 2017

Related U.S. Application Data

(60) Provisional application No. 62/294,478, filed on Feb. 12, 2016.

(51) Int. Cl.
*A61L 2/18* (2006.01)
*A61L 29/16* (2006.01)
(Continued)

(52) U.S. Cl.
CPC ............ *A61L 29/16* (2013.01); *A61L 2/0088* (2013.01); *A61L 29/14* (2013.01); *A61L 33/00* (2013.01);
(Continued)

(58) Field of Classification Search
CPC ................................ A61L 29/16; A61L 2/0088
See application file for complete search history.

(56) References Cited

U.S. PATENT DOCUMENTS

| | | | |
|---|---|---|---|
| 6,679,870 B1 * | 1/2004 | Finch | A61L 2/18 514/222.5 |
| 8,226,971 B2 | 7/2012 | Ash et al. | |

(Continued)

FOREIGN PATENT DOCUMENTS

| | | |
|---|---|---|
| JP | 2002523336 A | 7/2002 |
| JP | 2004516041 A | 6/2004 |

(Continued)

OTHER PUBLICATIONS

Ghigo, J.M. (Jul. 26, 2001). "Natural conjugative plasmids induce bacterial biofilm development," Nature 412: 442-445.

(Continued)

*Primary Examiner* — Donald R Spamer

(57) ABSTRACT

Various embodiments relate to catheter locking solutions and catheter locking therapies with use of trisodium citrate and ethyl alcohol, and in particular 4.0 to 15.0 weight/volume % trisodium citrate as an anticoagulant component and/or an antibacterial component and 15.0 to 25.0 volume/volume % ethyl alcohol as an antibacterial component. Use of the catheter locking solution and catheter locking therapy can reduce treatment failure during medical procedures that may employ catheters to supply treatment by at least significantly reducing the risks associated with bloodstream infections, catheter system malfunction, emboli formation, patient discomfort, and patient illness. These benefits can be partially due to the synergistic antibacterial effects of the trisodium citrate and ethyl alcohol in solution, generating an effective catheter locking solution with minimal concentrations of ethyl alcohol.

13 Claims, 6 Drawing Sheets

(51) Int. Cl.
*A61L 29/14* (2006.01)
*A61L 33/00* (2006.01)
*A61L 2/00* (2006.01)
*A61M 25/00* (2006.01)

(52) U.S. Cl.
CPC ..... *A61L 2300/21* (2013.01); *A61L 2300/216* (2013.01); *A61L 2300/404* (2013.01); *A61L 2300/42* (2013.01); *A61M 25/0017* (2013.01); *A61M 2025/0019* (2013.01)

(56) References Cited

U.S. PATENT DOCUMENTS

| | | | |
|---|---|---|---|
| 2003/0144362 | A1 | 7/2003 | Utterberg et al. |
| 2005/0136118 | A1 | 6/2005 | Wu et al. |
| 2005/0215978 | A1* | 9/2005 | Ash ............... A61M 25/00 604/508 |
| 2010/0318040 | A1* | 12/2010 | Kelley, III ......... A61K 9/0019 604/265 |
| 2013/0231302 | A1 | 9/2013 | Raad et al. |
| 2014/0371171 | A1 | 12/2014 | Souweine |
| 2015/0148287 | A1 | 5/2015 | Woo et al. |

FOREIGN PATENT DOCUMENTS

| | | |
|---|---|---|
| KZ | 26762 A4 | 4/2013 |
| RU | 2399375 C2 | 9/2010 |
| RU | 2471508 C2 | 1/2013 |
| RU | 2012145021 A1 | 4/2014 |
| SU | 1097336 A1 | 6/1984 |
| TW | 200520746 | 7/2005 |
| WO | 00/10385 A1 | 3/2000 |
| WO | 01/85249 | 11/2001 |
| WO | 2012/018437 | 2/2012 |
| WO | 2015/077798 | 5/2015 |
| WO | 2002/005188 A1 | 1/2020 |

OTHER PUBLICATIONS

Takla et al., "Effectiveness of a 30% ethanol/4% trisodium citrate locking solution in preventing biofilm formation by organisms causing haemodialysis catheter-related infections," *J. Antimicrobial Chemotherapy* (2008) 62, pp. 1024-1026.

Bell, A.L. et al., "Ethanol/Trisodium Citrate for Hemodialysis Catheter Lock," Clinical Nephrology (May 2004), vol. 62(5), pp. 369-373.

* cited by examiner

CATHETER LOCKING SOLUTION AND CATHETER LOCKING THERAPY

BACKGROUND OF THE INVENTION

Field of the Invention

Embodiments of the presently disclosed invention relate to catheter locking solutions and catheter locking therapies with use of trisodium citrate and ethyl alcohol, and in particular 4.0 to 15.0 weight/volume % tri sodium citrate as an anticoagulant component and/or an antibacterial component and 15.0 to 25.0 volume/volume % ethyl alcohol as an antibacterial component.

Background of the Related Art

Catheters are tubular objects that can be inserted into the body of a patient for supplying various treatments. Intravascular catheters are a common form of catheter used to supply treatment through vessels of the body. Such treatments can include hemodialysis, intravascular cooling, intravascular ultrasound, etc. Yet, catheterization and treatments ensuing catheterization can be associated with many risks. For example, biofilm generation due to pathogenic bacteria growth and/or fungi growth in, on, and/or around the catheter can occur. Biofilm generation can lead to blood clot formation, as well as bloodstream infections. Thrombus formation and/or emboli formation can also occur in, on, and/or around the catheter. For example, blood clot formation can spawn from endothelial trauma and inflammation due to the catheterization process. Another risk can come from precipitation of solids from solutions used within the catheter system. Biofilm generation, blood clot formation, and/or precipitation of solids can result in catheter malfunction, such as catheter occlusion for example. Furthermore, any of these conditions can further lead to potential health hazards for the patient.

A common method for reducing risks associated with catheterization and treatments ensuing catheterization can be catheter locking therapy, wherein a catheter locking solution (e.g., antibacterial and/or anticoagulant solutions) may be introduced into the catheter's lumen. Catheter locking solutions and catheter locking therapies may be used to reduce the proclivity of occurrence of any of the above-mentioned conditions and/or mitigate the effects thereof. Generally, a catheter locking solution is introduced into the catheter system in between usage sessions to reduce bacteria formation and thrombus formation, and thus moderate biofilm generation and catheter malfunction. Conventional catheter locking solutions may include antibacterial agents to reduce bacteremia and anticoagulant agents to reduce any likelihood of catheter malfunction.

One of the deficiencies with existing solutions and therapies is their failure to effectively reduce the tendencies leading to catheter malfunction. Another failure is their inability to effectively reduce the tendencies leading to catheter malfunction while also reducing the effects that may lead to patient discomfort and patient illness. Further, many existing catheter locking solutions are incapable of preventing catheter malfunction without having adverse effects on the catheter system. For example, existing solutions may rely on antibiotic agents to generate antibacterial effects. This can lead to an increase in antimicrobial resistance, which can be adverse to a patient, especially for patients engaged with chronic use of the catheter system. Other solutions may generate antibacterial and/or anticoagulant effects via use of agents that produce a toxic environment to a patient, leading to discomfort, illness, and other complications. Further, many solutions are deleterious to the catheter system, causing material degradation and acting as a catalyst for shortened service life of the component parts of the catheter system.

Generally, existing catheter locking solutions have forced practitioners to select a catheter locking therapy that is a trade-off from one desired effect in favor of another. For example, existing catheter locking solutions may consist of components that are either better for antibacterial functions or better for anticoagulant functions, where the combination of such components fails to exhibit any type of synergistic effect mitigating the trade-off. As another example, other existing catheter locking solutions can exhibit good antibacterial effects, but cause discomfort for a patient or have a deleterious effect on the catheter.

Embodiments of the presently disclosed invention are directed towards overcoming one or more of the above-identified problems.

BRIEF SUMMARY OF THE INVENTION

The disclosed catheter locking solution can include 4.0 to 15.0 weight/volume % ("w/v %") trisodium citrate. Trisodium citrate may be used as an anticoagulant component and/or an antibacterial component of the catheter locking solution. The catheter locking solution can further include 15.0 to 25.0 v/v % ethyl alcohol. Ethyl alcohol may be used as an antibacterial component of the catheter locking solution. Some embodiments can include a catheter locking solution comprising an aqueous solution containing 4.0 to 15.0 w/v % trisodium citrate and 15.0 to 25.0 v/v % ethyl alcohol ("TCEA solution"). Other ratios within the range can include 10.0 w/v % trisodium citrate and 20.0 v/v % ethyl alcohol, which may generate a relatively milder antimicrobial locking solution. As another example, 10.0 w/v % trisodium citrate and 25.0 v/v % ethyl alcohol may be used to generate a relatively stronger anti-microbial effect locking solution.

It is contemplated for the presently disclosed invention to be used with a catheter system, which can be an indwelling catheter system or a "permanent" catheter system. A typical catheter system can include a tubular shaft having a tip with a lumen formed therein, a hub connector, a flashback chamber, a grip portion, and a needle. More or less pieces of the catheter system can be used. For example, the presently disclosed invention may be used with a catheter system consisting essentially of the tubular shaft. As another example, the catheter system can include additional components, such as a filter, a bladder, etc. While the presently disclosed invention may be described herein as being used with a catheter system, it is certainly not limited to such use. The catheter locking solution and catheter locking therapy can be used for any situation where it is desired to generate an environment that is free, or substantially free, from biofilm growth and/or blood coagulation. For example, a method of use can include a method of treating for biofilm by introducing a solution including trisodium citrate and ethyl alcohol to a targeted environment and maintaining contact between the trisodium citrate and ethyl alcohol solution and the targeted environment to at least one of prevent biofilm generation and eradicate biofilm that has been generated at the targeted environment.

Embodiments of the catheter locking solution can be used to reduce treatment failure during medical procedures that may employ catheters to supply treatment. This may be achieved through use of any of the disclosed embodiments of the catheter locking solution and/or any of the disclosed embodiments of the catheter locking therapy. Thus, the catheter locking solution and/or the catheter locking therapy can be used to prevent generation of biofilm and/or completely eradicate biofilm that has generated within a catheter system. For example, preliminary in vitro testing shows that trisodium citrate alone at a concentration of 10.0 w/v % had no effect on the bacterial survival. Ethyl alcohol at a concentration of 15.0 v/v % decreased bacterial cells from 1.00 E+07 to 1.00E+02 and did not lyse all bacterial cells. Trisodium citrate, alone, does not inhibited or provide for an adequate agent to lyse bacterial cells. Yet, the combination of ethanol at a concentration of 15.0 v/v % with trisodium citrate at a concentration of 10.0 w/v % induced a complete lysis of the bacterial cells (under the threshold of detection). Further, a same or similar dosage can inhibit or prevent coagulation by citrate ion chelating calcium ions in the blood to interrupt blood clotting.

In some embodiments, the catheter locking solution can be introduced into the lumen of a catheter when the catheter is not being used to supply treatment and/or when the catheter is not inserted into a body of a patient. For example, the catheter locking solution can be used between dialysis sessions of a catheter system being employed for hemodialysis. The catheter locking solution can be left to reside within the lumen (i.e., dwell within the lumen) for the duration that the catheter is not in use and/or not inserted into the patient. In some embodiments, the catheter locking solution can be left to reside in the lumen for a predetermined period of time, regardless of how long the catheter will not be in use and/or remains outside of the patient.

Use of a catheter locking solution comprising at least the TCEA solution can nearly eradicate, or completely eradicate, biofilm existing within the lumen. Such a solution can also prevent biofilm generation. Further, such a solution may be used with little to no material degradation to the catheter material caused by the catheter locking solution. Catheter locking solutions with at least some TCEA solution can be generated exhibiting a pH that is salutary to the catheter, thus further limiting deleterious effects to the catheter material. Furthermore, the TCEA solution may generate additional benefits to the catheter system and/or patient by not causing plasma protein precipitation, not causing patient discomfort, significantly reducing catheter malfunction, and having the capability to be used with catheter locking therapies excluding the use of glyceryl trinitrates ("GTNs"). As will be explained in detail below, the various embodiments of the catheter locking solutions and the catheter locking therapies can prevent, or at least significantly reduce, the risks associated with bloodstream infections, catheter system malfunction, emboli formation, patient discomfort, and patient illness. Furthermore, catheter locking solutions with at least some TCEA solution can provide a trisodium citrate component as an anticoagulant agent and/or an antibacterial agent, while tri sodium citrate within the disclosed ranges to generate TCEA can generate the unexpected result of boosting the anti-microbial effect of ethyl alcohol.

Further embodiments of the presently disclosed invention can be used in conjunction with other catheter locking agents and catheter locking therapies. These may include, but are not limited to, thrombolytic agents, heparin solutions, saline solutions, hydrochloric acid solutions, other chelating agents, other alcohols, other biofilm disrupters, flushing techniques, positive pressure techniques, fibrinolytic therapies etc. It is noted that use of other catheter locking solution agents, such as heparin for example, may stimulate adherence of biofilm to a surface of the catheter, and thus caution should be exercised when employing the TCEA solution in conjunction with other catheter locking solution agents. Other side effects of heparin can include increased bleeding, skin rash, headache, cold symptoms, and stomach upset. A less common side effect may be loss of bone strength if patients are subjected to heparin for long periods of time (e.g., durations lasting a few months or more). These side effects may be exacerbated during use with patients who are pregnant. A rare side effect of heparin is a condition called Heparin Induced Thrombocytopenia ("HIT"). HIT is sometimes incorrectly called "heparin allergy." HIT is an autoimmune process with development of low platelet count. It occurs in a small number of patients (approximately 3-5% of patients subjected to heparin treatment), but it has very serious symptoms, including worsening of clotting and the development of new clots, which can lead to stroke, heart attack, deep vein thrombosis, and death.

While these potential advantages are made possible by technical solutions offered herein, they are not required to be achieved. The presently disclosed catheter locking solutions and catheter locking solution therapies can be implemented to achieve technical advantages, whether or not these potential advantages, individually or in combination, are sought or achieved.

Further features, aspects, objects, advantages, and possible applications of the present invention will become apparent from a study of the exemplary embodiments and examples described below, in combination with the Figures, and the appended claims.

BRIEF DESCRIPTION OF THE DRAWINGS

The above and other objects, aspects, features, advantages and possible applications of the present invention will be more apparent from the following more particular description thereof, presented in conjunction with the following drawings, in which:

FIG. 3A shows the change in pH, FIG. 3B shows the change in RI, FIG. 3C shows the change in density, and FIG. 3D shows the weight loss.

DETAILED DESCRIPTION OF THE INVENTION

The following description is of an embodiment presently contemplated for carrying out the present invention. This description is not to be taken in a limiting sense, but is made merely for the purpose of describing the general principles and features of the present invention. The scope of the present invention should be determined with reference to the claims.

It is contemplated for the catheter locking solution to be employed via Water for Injection ("WFI"), and thus the catheter locking solution may be an aqueous solution. It is further contemplated for approximately 75% of the solution to include water. Embodiments of the disclosed catheter locking solution can include trisodium citrate in aqueous solution. Other embodiments of the catheter locking solution can include ethyl alcohol in aqueous solution. Some embodiments can include trisodium citrate and ethyl alcohol in aqueous solution. An exemplary embodiment is referred to herein as the "TCEA solution," which may include an aqueous solution comprising trisodium citrate having a concentration within a range from 4.0 to 15.0 weight/volume % ("w/v %") and ethyl alcohol having a concentration within a range from 15.0 to 25.0 volume/volume % ("v/v %"). Concentrations of trisodium citrate are measured in weight of trisodium citrate per total volume of the solution. Concentrations of ethyl alcohol are measured in the volume of ethanol per the total volume of the solution. Within the various embodiments, the trisodium citrate component may be used as an anticoagulant agent and/or an antibacterial agent. Furthermore, the ethyl alcohol component may be used as an antibacterial agent. When referring to an antibacterial effect within this disclosure, it is understood that this effect also encompasses antimicrobial effects, antibiotic effects, antifungal effects, and antiseptic effects.

Figure 1:
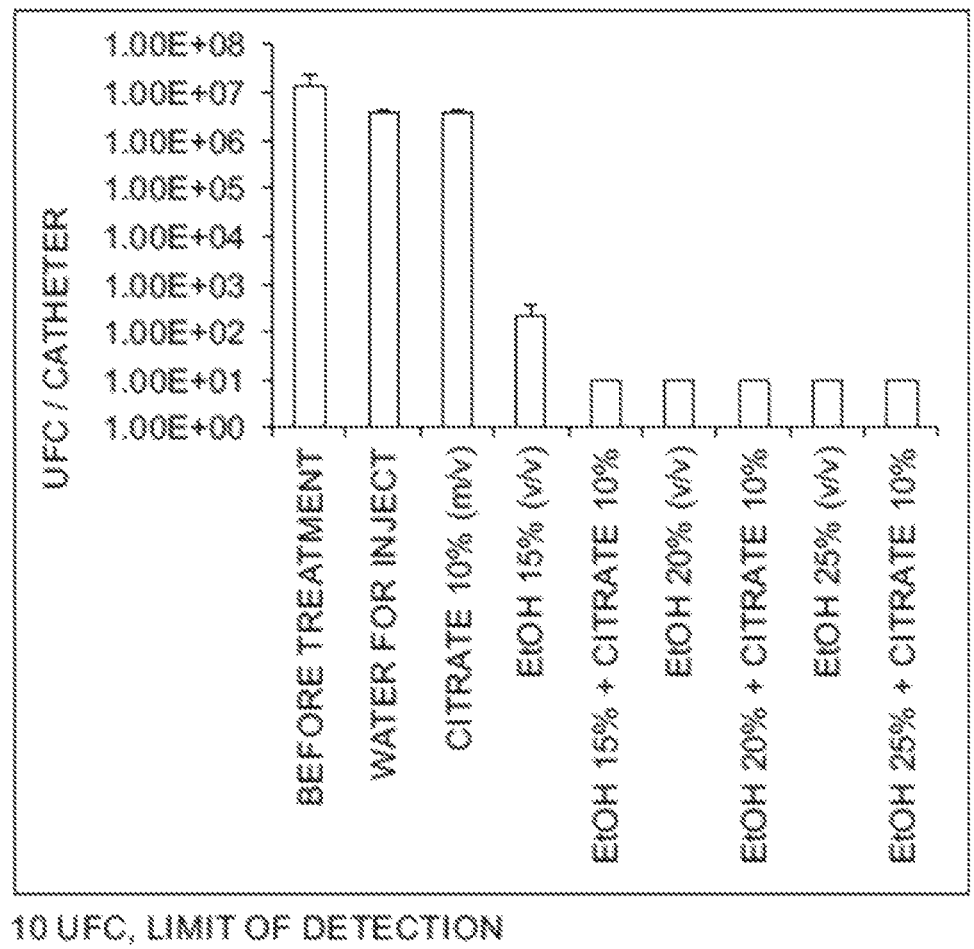
FIG. 1 is a graph depicting test results related to the antibacterial synergistic effects of trisodium citrate and ethyl alcohol in solution, and in particular a graph of the colony forming units of bacterial strain as a function of solutions having various concentrations of trisodium citrate and ethyl alcohol.

Referring to FIG. 1, it is seen that a catheter locking solution with an aqueous solution containing a concentration of trisodium citrate within a range from 4.0 to 15.0 w/v % has a minor antibacterial effect. A catheter locking solution with an aqueous solution containing a concentration of ethyl alcohol within a range from 15.0 to 25.0 v/v % also has a minor antibacterial effect. However, a catheter locking solution comprising at least the TCEA solution has a significant antibacterial effect, and can nearly eradicate, or completely eradicate, biofilm within an environment maintaining contact with the TCEA solution for a predetermined period of time. It should be noted that the trisodium citrate component may be used as an anticoagulant agent and/or an antibacterial agent. Further, the use of trisodium citrate within the disclosed ranges to generate TCEA can generate the unexpected result of boosting the anti-microbial effect of ethyl alcohol.

The graph in FIG. 1 shows results of test data revealing the synergistic antibacterial effects of trisodium citrate and ethyl alcohol when forming the TCEA solution. For example, preliminary assay testing of anti-biofilm properties of a TCEA solution comprising a 10.0 w/v % concentration of trisodium citrate at and 15.0, 20.0 and 25.0 v/v % concentrations of ethyl alcohol (i.e., ethanol or EtOH) were conducted. The testing was performed in the following manner.

Test Solutions
Ethanol 15%, 20% and 25% (v/v)+trisodium citrate 10% (w/v)
  Controls: Ethanol 15%, 20% and 25%
  Trisodium citrate 10%
  Water for injection
The material tested were segments, each 1 centimeter long, of sterile catheters Chronoflex ("catheter segments"). The strains used were *Staphylococcus aureus* CIP 65.25 (methicillin resistant).
  Study Design
  Biofilms were formed in aerated microfermentors with catheter segments fixed onto an internal removable glass slide of the microfermentors. Strains from frozen stocks were cultivated in Trypticase Soja broth ("TSB"). An inoculum of $10^8$ cells was used to inoculate microfermentors containing the catheter segments. A continuous flow of 54 milliliters per hour ("mL/h") of TSB and constant aeration with sterile pressed air at 0.3 bar were used to obtain continuous flow-through culture conditions. After 24 hours of incubation, the catheter segments were removed from the incubator and separated from their respective microfermentor device. Each catheter segment was then carefully rinsed in 1 mL of saline.

To determine the number of viable cells within the biofilms formed onto the catheter segments before being subjected to or made to be in contact with the test solutions (i.e., before treatment), the biofilms (triplicate for each strain) were resuspended in TSB by sonication and vortexing. Serial dilutions of the resulting suspensions were performed and plated onto appropriate agar plates to determine the number of viable cells after overnight incubation at 37 degrees Celsius ("° C.").

In parallel, catheter segments to be tested were placed in a tube containing 1 mL of the different lock solutions: (i) ethanol at 15%, 20% and 25% (vol/vol); (ii) trisodium citrate at 10% (vol/vol); (iii) ethanol/tri sodium citrate mixing solutions (15%-10%, 20%-10%, 25%-10% (vol/vol)), wherein ethanol concentrations were 15%, 20%, and 25%, and trisodium citrate concentration was 10%; and (iv) water for injection as control. For every organism, the experiments were repeated in triplicate, and during each treatment assay catheter segments were exposed to the different solutions for 24 hours at 37° C. Subsequently, the catheter segments were removed, rinsed once with saline, and the number of adherent viable microorganisms determined, as described above. In FIG. 1, the number of viable cells is expressed as Colony Forming Unit ("CFU"), and the bacteria count is expressed as a decimal logarithm, log 10. (Note: FIG. 1 expresses the CFU as UFC, which is an acronym for unite formant colonie and is the same unit of measure as CFU.). The limit of detection in the experimental conditions is 10 CFU per KT segment, thus the threshold of detection is 10 CFU per KT segment. KT is a catheter sample used during testing, and its length can range from 3 to 5 centimeters. A KT can be a specimen of a catheter that have been cut (1 meter long usually) and placed into a microfermentor apparatus so that biofilms are formed at a surface of the catheter. Once the biofilm is formed and place into contact with the catheter lock solution to be tested, a measured the number of bacterial viable cells still present at the surface of the catheter is obtained. The limit of detection is 10 Colony Forming Units per specimen of catheter.

Results

TABLE I

|  | Moyenne | Ecart-type |
| --- | --- | --- |
| Before treatment | 1.30E+07 | 9.72E+06 |
| Water for Inject | 3.64E+06 | 3.80E+05 |
| citrate 10% (m/v) | 3.64E+06 | 3.80E+05 |
| EtOH 15% (v/v) | 2.12E+02 | 1.46E+02 |
| EtOH 15% + cit 10% | 1.00E+01 |  |
| EtOH 20% (v/v) | 1.00E+01 |  |
| EtOH 20% + cit 10% | 1.00E+01 |  |
| EtOH 25% (v/v) | 1.00E+01 |  |
| EtOH 25% + cit 10% | 1.00E+01 |  |

Note:
Ethanol is represented as EtOH; trisodium citrate is represented as citrate or cit.

It is clear from the data presented in Table I and FIG. 1 that trisodium citrate alone, at 10.0 w/v/% concentration, had no effect on the bacterial survival. Furthermore, EtOH alone, at 15 v/v % concentration, did not lyse all the bacterial cells. Yet, EtOH, at 15, 20, and 25 v/v % concentrations, mixed with trisodium citrate, at 10 w/v % concentration, induced a complete lysis of the bacterial cells. Note, the threshold of detection is 10 CFU per KT segment, thus the observance of complete lysis of the bacterial cells is under this threshold of detection. Results from the preliminary testing suggests that there is no significant difference between 20 v/v % and 25 v/v % of EtOH in-vitro. However, in actual clinical practice, due to leakage, evaporation, etc., a higher concentration of EtOH may generate an incrementally greater anti-microbial effect. For example, use of 20 v/v % and 25 v/v % of EtOH has resulted in a significantly greater effect in lysing the bacteria that use of 15 v/v % EtOH. There does not seem to be a significant difference between the use of 20 v/v % and 25 v/v % of EtOH alone in lysing bacteria.

An environment maintaining contact with the catheter locking solution, which may include the TCEA solution, for the predetermined period of time can be referred to as a targeted environment. The targeted environment may be within at least a portion of a catheter system, e.g., within a lumen of the catheter system. Table I shows that nearly all of pathogenic bacteria and/or fungi that has been generated within the lumen of the catheter can be killed after coming into contact with the TCEA solution, thereby nearly eradicating, or completely eradicating, biofilm comprising the bacterial and/or the fungi. The catheter locking solution has both anti-coagulation and anti-microbial effect as opposed to some existing catheter locking solutions and therapies that use Heparin alone or low to high concentrations of trisodium citrate alone. Higher concentrations of trisodium citrate can have the anti-microbial effect, but may have greater side effects for patient as compared to the presently disclosed catheter locking solution.

The beneficial effects of the currently disclosed catheter locking solution may be attributed to the ethyl alcohol component being able to penetrate the biofilm and kill microorganisms, fungi, and other pathogens by protein denaturation. While it is noted that ethyl alcohol may exhibit an antibiotic effect, ethyl alcohol is not an antibiotic. Thus, use of ethyl alcohol does not increase antimicrobial resistance. Examples of microorganisms killed by ethyl alcohol may include, but are not limited to, *S. aureus, S. epidermidis, Klebsiella pneumoniae, P. aeruginosa* and *Candida* spp., etc. Further, a same or similar dosage can prevent, or at least inhibit, coagulation by citrate ion chelating calcium ions in the blood to interrupt blood clotting.

As described above, the combined use of trisodium citrate and ethyl alcohol at such concentrations to form the TCEA solution generates the unexpected result of nearly eradicating, or completely eradicating, biofilm and/or preventing at least any significant formation of biofilm within the targeted environment. For example, those skilled in the art would not expect ethyl alcohol concentrations as low as 25.0 v/v % to exhibit effective antibacterial effects, let alone effective antibacterial effects with ethyl alcohol concentrations lower than 25.0 v/v %. Furthermore, as shown above, test results with various combinations of trisodium citrate and ethyl alcohol do not exhibit a nonlinear relationship associated with the compounding of the two minor antibacterial effects, and in particular any nonlinear relationship to suggest that any combination would result in a significant antibacterial effect. Further, no known theories of microbiology or chemistry suggest synergistic effects associated with antibacterial properties when combining trisodium citrate with ethyl alcohol in such a manner.

A catheter locking solution with ethyl alcohol concentrations as low as, or lower than, 25.0 v/v % may also be more salutary for the catheter. Ethyl alcohol can cause material degradation of materials commonly used to fabricate catheters (e.g., silicone, polyurethane, polyethylene, polytetrafluoroethylene, carbothane, etc.). The inventors have discovered that solutions with concentrations of at least 70 v/v % of ethyl alcohol have caused material degradation effects on catheter materials. Therefore, lower concentrations of ethyl alcohol may be better from a material degradation standpoint. For example, use of a catheter locking solution with ethyl alcohol concentrations as low as, or lower than, 25.0 v/v % may not cause material degradation at all, or at least not cause material degradation so as to reduce the service life of the catheter. Minimizing, or even preventing, material degradation due to the catheter locking solution can sustain the material integrity and mechanical integrity of the catheter system, and thus not generate unexpected strain on the catheter system.

A catheter locking solution with ethyl alcohol concentrations as low as, or lower than, 25.0 v/v % may be further beneficial to the catheter system and/or patient because ethyl alcohol concentrations higher than 25.0 v/v % may tend to cause generation of plasma protein precipitation, the generation of plasma protein precipitation leading to increased risk of catheter malfunction and/or emboli formation. Further, use of ethyl alcohol concentrations higher than 25.0 v/v % can cause other side effects, such as patient discomfort and illness (e.g., nausea, headache, taste of alcohol, respiratory distress, etc.)

The TCEA solution can be further used to generate a catheter locking solution exhibiting a pH level within a range from 4.0 to 8.0, which may also be salutary for the catheter system, as solutions having pH levels outside of this range can cause material degradation of the catheter material and increase the risk of unexpected strain on the catheter system. Furthermore, pH levels outside of the range of 4.0 to 8.0 can lead to induced precipitation, which can generate malfunctioning of the catheter system and/or potential hazards for the patient.

The TCEA solution may be further used to generate a catheter locking solution without the addition of glyceryl trinitrates ("GTNs"). For example, trisodium citrate is partially insoluble in ethyl alcohol, thus the use of GTN may not be necessary to inhibit and/or reduce trisodium citrate precipitate formation in the catheter locking solution having an ethyl alcohol concentration within the range from 15.0 to 25.0 v/v %. Thus, a catheter locking solution can be generated without the risk of trisodium citrate precipitation, wherein the catheter locking solution has at most 25.0 w/v % of ethyl alcohol and is free of GTNs. In other words, the catheter locking solution comprising at least some TCEA solution can be used as an antibacterial agent and/or an anticoagulant agent exhibiting any one or all of the benefits described herein at the targeted environment, wherein the targeted environment is free from GTNs or at least free from GTNs that would be added to prevent precipitate formation. A benefit of not including GTNs can be to generate a catheter locking solution with less components. This may lead to greater economic value for the same treatment effect. Furthermore, some individuals exhibit allergic reactions to GTN, the effects of GTN on catheter material and properties are unknown, and manufacturing of GTN can be difficult.

An exemplary study conducted by the inventors investigated the stability of the catheter locking solution including 10.0 w/v % trisodium citrate and 25.0% ethyl alcohol. Further, accelerated age test had been conducted with the same component ratios. Trisodium citrate can be highly effective at preventing catheter thrombosis (i.e., can be an effective anticoagulant agent). In preparing the catheter locking solution, the inventors have discovered that lower concentrations of trisodium citrate solution can be more soluble in ethyl alcohol. Further, trisodium citrate solutions having concentrations between 30.0 w/v % and 46.7 w/v % can significantly decrease bacterial cells growth (i.e., can be an effective antibacterial agent), but may not eradicate bacteria. Ethyl alcohol solutions having a concentration of 25.0 v/v % can suppress, but may not eradicate, mature biofilms (e.g., *S. aureus*). Ethyl alcohol solutions having a concentration above 40.0% can inhibit bacterial growth (i.e., can be an effective antibacterial agent). Ethyl alcohol solutions having a concentration above 60.0% can achieve total eradication of viable bacterial. The rapid killing rate of bacteria by ethyl alcohol can be exploited to prevent bacteria from becoming established on a surface of catheters, and thus prevent biofilm growth.

Figure 2:
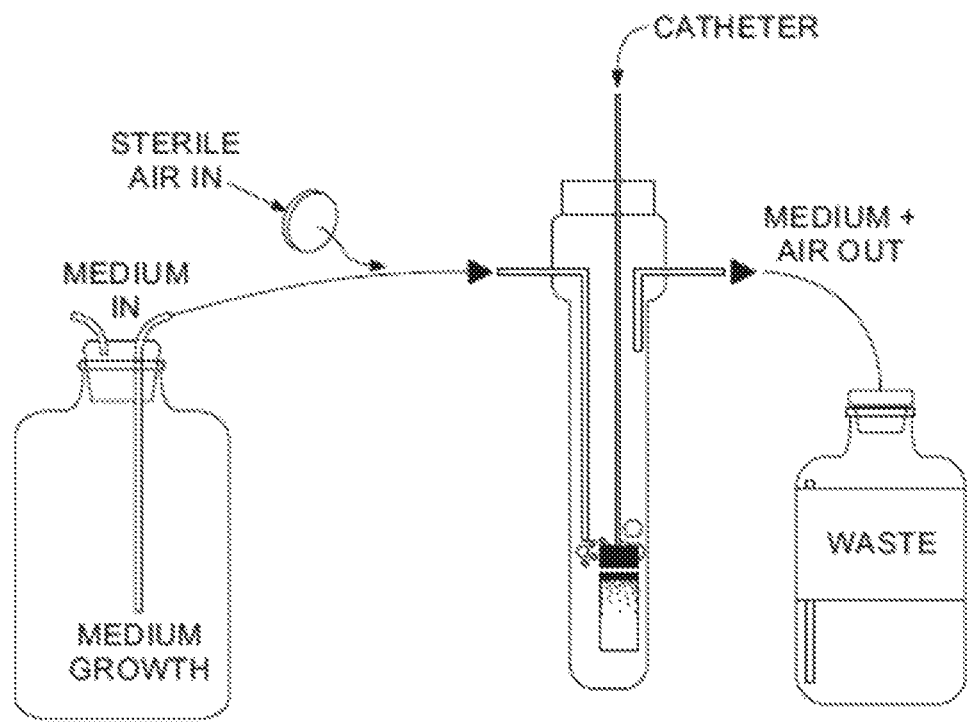
FIG. 2 is an exemplary experimental set up for ascertaining whether an exemplary catheter locking solution can eradication viable bacterial and prevent regrowth of biofilm.
Figure 3A:
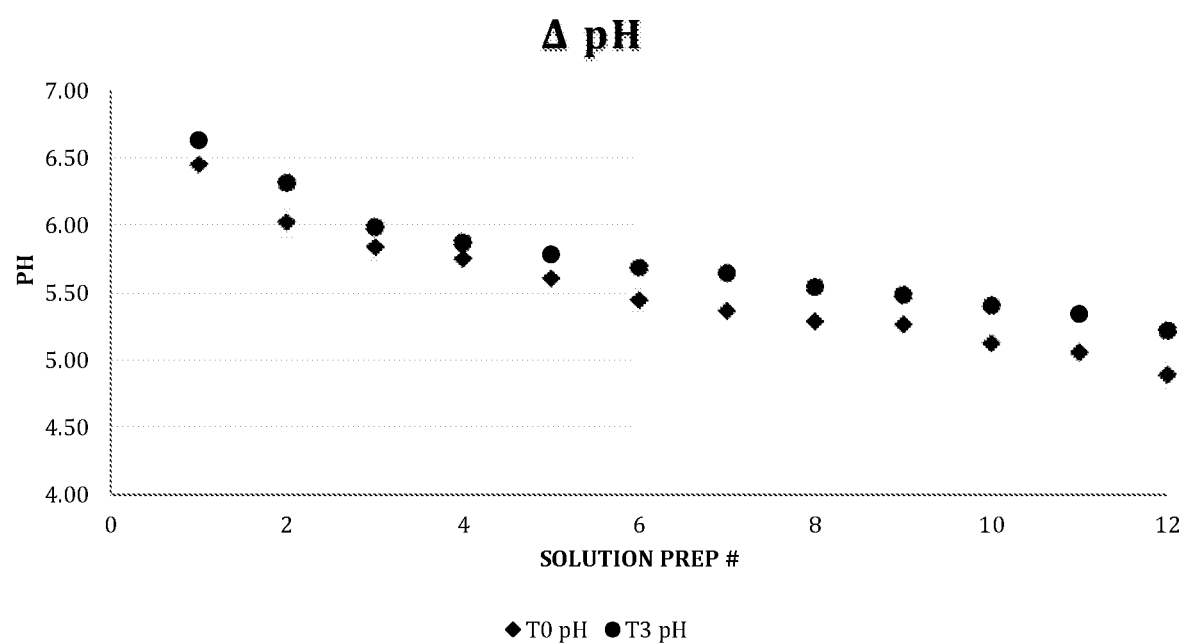
FIGS. 3A-3D show stability results of twelve exemplary formulated solutions during an exemplary accelerated age study, where
Figure 3B:
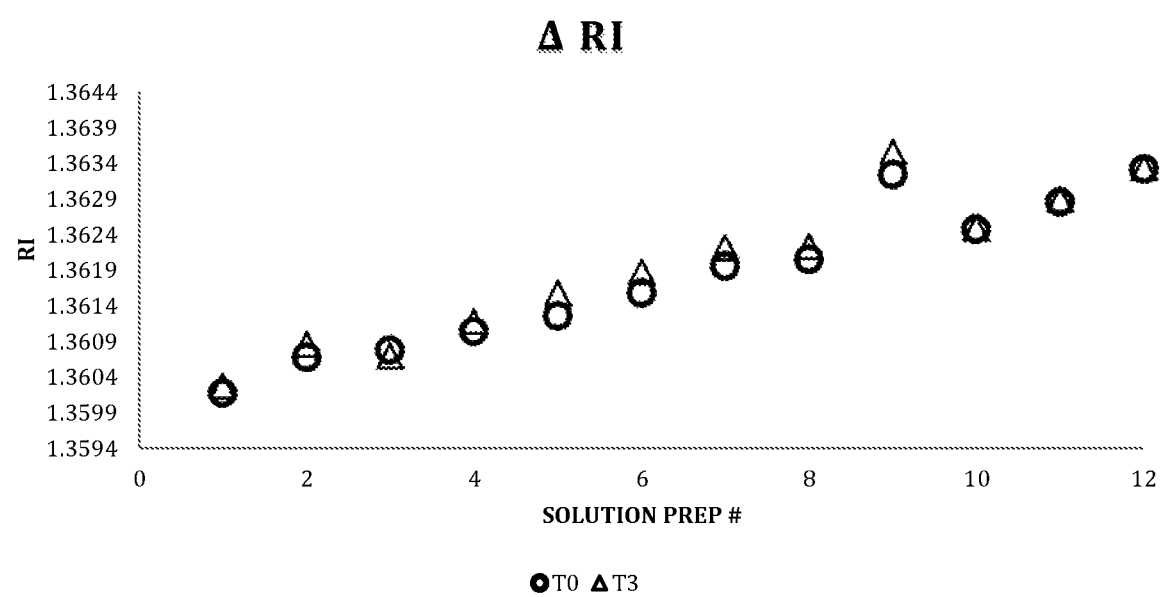
Figure 3C:
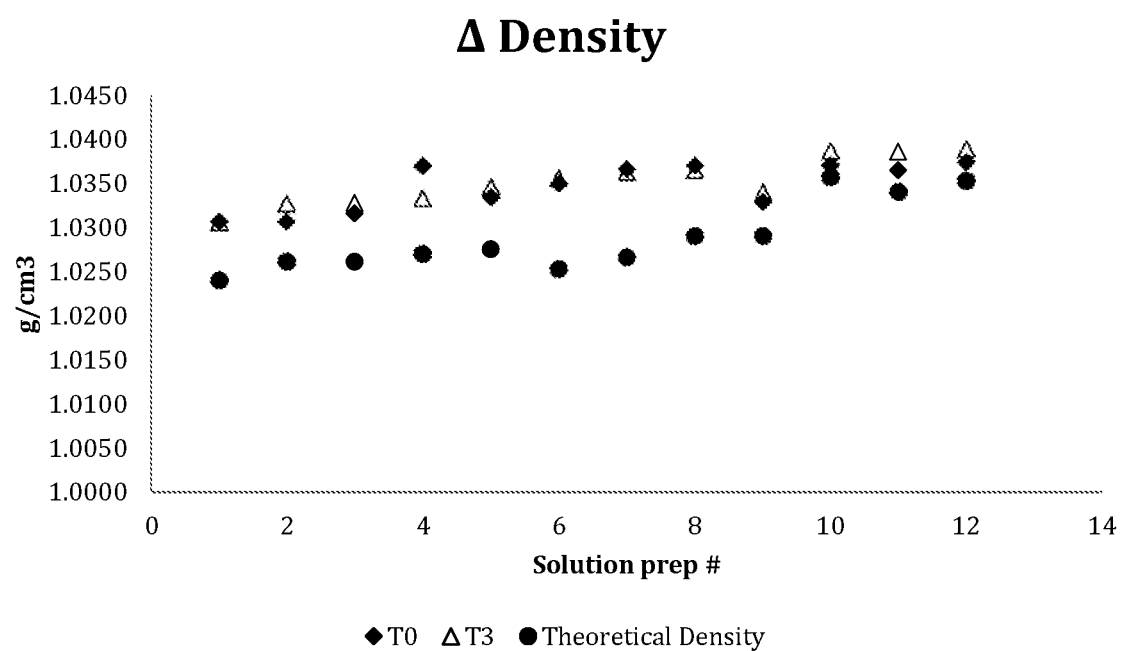
Figure 3D:
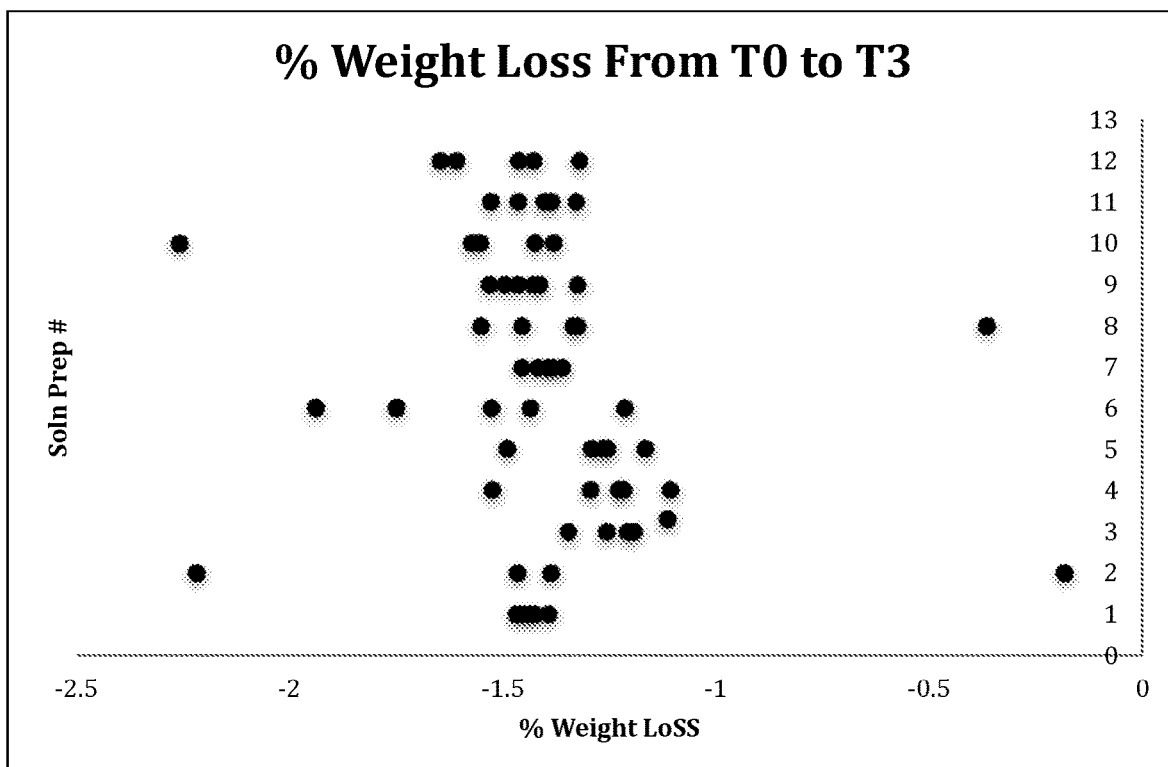

During the study, the disclosed catheter locking solution had been tested to ascertain whether it can eradication viable bacterial and prevent regrowth of biofilm. (See FIG. 2). The catheter locking solution had been tested against *Staphylococcus aureus* (methicillin resistant). Solutions with Trisodium citrate alone (at 10 w/v %) had no effect on the bacterial survival. Solutions with EtOH alone (at 15 v/v %) did not lyse all the bacterial cells. Solutions including a mixture of EtOH (at 15 v/v %) mixed with trisodium citrate (at 10 w/v %) induced a complete lysis of the bacterial cells (under the threshold of detection).

In an exemplary formulation, the inventors had prepared twelve solutions containing 10.0 w/v % trisodium citrate, 25.0 v/v % ethanol, and different amount of citric acid. Separate solutions containing 10.0 w/v % trisodium citrate (dissolved 25 grams of trisodium citrate in 125 milliliters of water and pH adjusted 5.0 to 7.0; Qsed to 250 milliliters with water) and 25.0 v/v % ethyl alcohol (added 125 milliliters of ethyl alcohol to a 500 milliliter VF and Qsed with water) had also been prepared as controls. pH levels and refractive index ("RI") levels had been measured at certain intervals throughout sample preparation, the results of which are presented in Table II.

TABLE II

| Sol. Prep | Concentration mg/mL | Volume Ethanol (mL) | Citric Acid (g) |
|---|---|---|---|
| 1 | 10 | 50 | 0.5 |
| 2 | 10 | 50 | 1 |
| 3 | 10 | 50 | 1.5 |
| 4 | 10 | 50 | 2 |
| 5 | 10 | 50 | 2.5 |
| 6 | 10 | 50 | 3 |
| 7 | 10 | 50 | 3.5 |
| 8 | 10 | 50 | 4 |
| 9 | 10 | 50 | 4.5 |
| 10 | 10 | 50 | 5 |
| 11 | 10 | 50 | 5.5 |
| 12 | 10 | 50 | 6 |

The procedure for the stability study with the exemplary formulations described above had been carried out as follows.

Syringe and Pouch Preparation:
 Manually filled syringe and torqued caps
 Used current packaging materials of DuraLock-C(Boxes/pouches)
 Labeled boxes/pouches
 Pouches contained 5/2.5 mL syringes
 Prepared a total of 25 syringe for each time point. Total of 75 syringes for each sample solution.
 Syringes: 1-15: Sanxin 3 mL syringes with red Sanxin caps
 Syringes: 16-25: BD 3 mL syringes with Vitalmed Blue caps
 Total of 15 pouches for each sample prep
 Pouches were sealed
Sterilized Samples:
 Samples were Gamma Sterilized
 After boxes returned pouches and samples were inspected for any precipitation
Placed Samples in Chamber (Condition):
 Samples placed in chamber at 40° C./NMT 25% RH
 Time point for accelerated aging are 0 months, 3 months, and 6 months
 Temperature and Humidity monitored in chamber
 T0=0 months, T3=3 months, T6=6 months Referring to FIGS. 3A-3D and Table III, the results of the twelve exemplary formulated solutions are disclosed. As can be seen, with the addition of trisodium citric acid, pH decreased, RI increases, and density increases. There is no statistical difference in density (the sum of mass concentration of components in the solution) from the T0 sample and the T3 samples. The appearance of the solutions was clear (i.e., the T0 samples and T3 samples had the same clarity as water). The extractable volume for the T0 samples was 25 out of 25 Pass, >2.5 mL. That of the T3 samples was 23 out of 25 Pass, >2.5 mL. The caps were not properly sealed and salt formed on exterior of cap. Thus, the results suggest that a solution of 10 w/v % of trisodium citrate and 25 v/v % ethanol remains stable and soluble after three months (Accelerated=1 yr Real Time).

TABLE III

| T0 pH | T3 pH | % Difference |
|---|---|---|
| 6.45 | 6.63 | 2.8 |
| 6.02 | 6.32 | 4.8 |
| 5.84 | 5.99 | 2.6 |
| 5.75 | 5.88 | 2.1 |
| 5.61 | 5.78 | 3.2 |
| 5.44 | 5.69 | 4.5 |
| 5.37 | 5.65 | 5.3 |
| 5.29 | 5.55 | 4.8 |
| 5.27 | 5.49 | 4.2 |
| 5.13 | 5.41 | 5.5 |
| 5.06 | 5.34 | 5.6 |
| 4.89 | 5.22 | 6.7 |

As described above, the various disclosed catheter locking solutions and the catheter locking therapies may be used to prevent or alleviate catheter malfunction. One form of catheter malfunction is formation of a catheter occlusion. Occlusions may occur at any time during catheterization and/or at any time during supplying treatment via the catheter system. For example, the catheter shaft inserted into the patient's body can become covered with plasma and fibrin, wherein platelets and white blood cells begin to adhere thereto, allowing for colonization of bacteria, more fibrin formation, blood clotting, and then a thrombus. Thrombus formation can occur within the lumen of the catheter, on the surface of the tip of the catheter, and/or within proximity of the tip of the catheter, thereby leading to catheter malfunction via occlusion. When formed on the surface, the occlusion-forming thrombus can adhere to an inside surface and/or an outside surface of the catheter system, wherein the thrombus obstructs flow within the catheter system. An occlusion within the catheter system can occur where blood and/or an existing emboli refluxes inside the lumen through the tip, leading to an obstruction of flow. Use of catheter locking solutions comprising TCEA can prevent, or at least significantly reduce the risk of, thrombus-style occlusions by inhibiting thrombus formation, as described above.

Occlusions can also occur from plasma protein precipitation, solid particle precipitation from components of a catheter locking solution, solid particle precipitation from constituents of a supply treatment used with the catheter system, and other precipitate forming mechanisms. These precipitates can cause occlusions in a similar fashion as described above. These precipitates, well as the thrombus formations, can also lead to potential hazards for a patient even if no occlusion is formed therefrom. For instance, a precipitate formation and/or a thrombus formation can enter the bloodstream and cause an emboli. Use of catheter locking solutions comprising TCEA can prevent, or at least significantly reduce the risk of, precipitate formation, as described above.

Disclosed are ranges of concentrations for each component of the TCEA solution. Ranges are disclosed because it is contemplated that relative concentrations of trisodium citrate and ethyl alcohol would provide various desired effects. For example, while a lesser concentration of ethyl alcohol may be generally more beneficial for reducing strain on the catheter system, reducing risk of precipitation, and reducing other side effects, ethyl alcohol exhibits broad effectiveness in killing many types of microorganisms without such organisms developing an antimicrobial resistance thereto. Thus, a concentration of ethyl alcohol near the top of the range (e.g., near 25.0 v/v %) may be desired to maximize antibacterial effects, whereas a concentration of ethyl alcohol near the bottom of the range (e.g., near 15.0 v/v %) may be desired to minimize patient discomfort or catheter system strain. Other relative component concentrations may be utilized to accommodate the patient's condition and the type of catheter system.

As an example, ratios within the range can include 10.0 w/v % trisodium citrate and 20.0 v/v % ethyl alcohol, which may generate a relatively milder anti-microbial locking solution. As another example, 10.0 w/v % trisodium citrate and 25.0 v/v % ethyl alcohol may be used to generate a relatively stronger anti-microbial effect locking solution.

A catheter locking therapy can include a method of use with the catheter locking solution to achieve any one of the desired effects at the targeted environment. The catheter locking therapy can include introduction of the catheter locking solution within the lumen, wherein the volume confined by the lumen and/or the interior surface of the lumen are the targeted environment. In some embodiments, the catheter locking solution may be introduced within the lumen while the catheter is not being used to supply treatment to the patient (e.g., between dialysis sessions of a catheter system being employed for hemodialysis). A catheter locking therapy can further include a flushing step, a positive pressure application step, etc.

As described above, the use of the catheter locking solution does not have to be limited to use with a catheter system. For example, a method of use can include a method of treating for biofilm by introducing a solution including trisodium citrate and ethyl alcohol to a targeted environment and maintaining contact between the trisodium citrate and ethyl alcohol solution and the targeted environment to at least one of prevent biofilm generation and eradicate biofilm that has been generated at the targeted environment.

In an exemplary embodiment, the catheter system can first be flushed with a volume of water, 0.9% sodium chloride in aqueous solution, or a saline solution to adequately remove debris, fibrin, precipitates, and other deposits (e.g., lipids, drugs, etc.) that may exist within the catheter system. The amount of flush fluid may be approximately 5.0 to 10 mL, but will generally depend on the catheter system and the conditions of the targeted environment. Thereafter, a volume of the catheter locking solution can be introduced into the catheter system, which may be limited to the lumen, limited to another portion of the catheter system, or be injected throughout the entire catheter system. The catheter locking solution can be made to reside (or dwell) at the targeted environment for a predetermined period of time. Alternatively, or in addition, the catheter locking solution can be made to reside at the targeted environment to maintain patency of the lumen, patency of the tip, and/or patency of another portion of the catheter system. Generally, this will depend on the targeted environment, the catheter system, and the relative components of the TCEA solution.

Generally, the volume of catheter locking solution used for a given catheter locking therapy may be an amount that would maintain sufficient contact with the targeted environment to achieve the desired result. This amount of catheter locking solution may be an amount that would ensure adequate contact between the catheter locking solution and the targeted environment is maintained for a predetermined period of time. For example, this amount of catheter locking solution may be an amount that would be enough to fill the entire lumen of the catheter, provided the lumen is the targeted environment. For example, 0.03 mL of catheter locking solution may be used to fill the lumen of a peripheral catheter, 0.4 mL of catheter locking solution may be used to fill the lumen of a 4 French midline catheter, etc. Further, if the entire catheter system, as opposed to just the lumen, is the targeted environment and the catheter system includes an additional piece (e.g., a venous access port), the volume of the port's reservoir and any other connecting parts of the port may be included. Further, if the catheter locking solution is able to leak from the catheter system, the catheter locking therapy can include injection of additional catheter locking solution to ensure adequate contact between the catheter locking solution and the targeted environment is maintained for the desired period of time. For example, if the lumen is the targeted environment and the catheter locking solution is able to leak from the targeted environment, an injection of an additional 15 to 20% catheter locking solution beyond the amount to fill the lumen can be performed.

The time period at which the catheter locking solution resides or dwells within the catheter system can depend on many factors. Generally, the time period will be the duration for which the catheter system is not being used to supply treatment. Using the catheter locking solution in such a fashion may be referred to as "locking the catheter." With a typical dialysis session, the time period between sessions may be 12 to 24 hours, and thus the catheter locking solution may dwell within the catheter system for such duration.

An additional flushing step may be performed after locking the catheter and/or before supply of treatment via the catheter system. For instance, the catheter locking solution can be aspirated from the catheter system via flushing techniques similarly described above. Aspiration can be done to "renew" the catheter locking solution (i.e., flush out the catheter locking solution and introduce more of the same or a different catheter locking solution). Aspiration can be further done to prepare the catheter system for supplying treatment to the patient (e.g., supplying a drug treatment). If the catheter locking solution can be introduced into the bloodstream without creating a risk of harm to the patient, then aspiration may not be performed (i.e., the catheter locking solution can be forced into the bloodstream of the patient as opposed to being removed from the catheter system without introduction into the bloodstream). Introduction of the TCEA solution into the bloodstream can be performed with minimal side effects to the patient, and thus aspiration may not be part of the catheter locking therapy if it is desired to not perform aspiration. This is because a catheter locking solution comprising TCEA solution may not significantly increase the risk of toxicity of the patient if released into the bloodstream of the patient.

While it is contemplated for the targeted environment to be within at least a portion the lumen of the catheter system, the targeted environment can be any portion of the catheter system (e.g., an outer surface of the catheter shaft, a filter portion, a bladder portion, a reservoir of a venous access port, etc.) and/or be a volume of space outside of the catheter system (e.g., within the body of the patient and outside of the catheter system). For example, the catheter locking solution can be toxic so a corresponding catheter locking therapy may be devised such as to prevent the catheter locking solution from entering the bloodstream by remaining within the catheter system unless controllably flushed (i.e., aspirated) from the catheter system. In some embodiments, the catheter locking therapy can be such that the catheter locking solution remains localized at a specific biofilm site, which can be a site within the catheter system (e.g., within the lumen, within the filter, etc.). In other embodiments, the catheter locking solution can be less toxic or even nontoxic so that a catheter locking therapy may be devised to permit at least a small amount of catheter locking solution to be introduced into the bloodstream (intentionally or inadvertently) without causing injury or harm to the patient. In further embodiments, the catheter locking therapy can be designed to cause catheter locking solution to enter the bloodstream so as to supply some form of treatment.

Further embodiments can include flushing, locking, aspiration, and/or renewal regimens. This may include renewal of the catheter locking solution at specified time periods, wherein a catheter system has been locked and has not been in use for an extended period of time. For example, with a typical dialysis session, a catheter system may be flushed after a dialysis session, then locked for a period of 12 to 24 hours while the catheter locking solution is renewed after every 8 hours, and then flushed again to prepare the catheter system for a subsequent treatment associated with dialysis after the locking period.

Further embodiments can include the catheter locking solution prefilled in sterilized syringes, wherein each syringe in a first set of syringes includes a first colored cap and each syringe in a second set of syringes includes a second colored cap. As an example, the first color may be red and the second color may be blue. The red cap(s) may be used to signify the syringe(s) intended for use with catheters designated for arterial lumens. The blue cap(s) may be used to signify the syringe(s) intended for use with catheters designated for venous lumens.

Further embodiments of the catheter locking therapy can include application of positive pressure in the catheter system to inhibit and/or prevent influx of blood or other material into the catheter system. For example, techniques can be employed to ensure that a positive differential pressure is exhibited within the catheter system before ceasing supply of treatment, thereby minimizing the risk of blood influx when the supply of treatment is stopped. The application of positive pressure can also be applied before and/or after each stage of a catheter locking therapy regimen.

Exemplary solutions will be tested to assess the antibiofilm properties of a mixture of ethanol 25% —citrate (from 5 to 15%) on biofilm formation and on mature biofilms using several representatives of pathogens. Tests for generating such results are provided in two Examples.

Example I

Solutions to be tested:
Ethanol 25% (vol/vol)+trisodium citrate 5%-10% and 15%
Controls: Ethanol 25%, trisodium citrate 5%, trisodium citrate 10%, trisodium citrate 15%, saline
Material to be tested:
Segments (each 1 cm long) of sterile catheters (Chronoflex™, Carbothane™, Silicone, Tecothane™ and Pellethane®).
Strains:
*Staphylococcus epidermidis* CIP 68.21
*Staphylococcus aureus* CIP 65.25 (methicillin resistant)
*Pseudomonas aeruginosa* ATCC 27853
*Klebsiella pneumoniae* LM21
*Candida albicans* SC5314

Bacterial strains are grown in lysogeny broth (LB) and in minimal medium (M63B1) and the fungal species in 0.67% yeast nitrogen base (Yeast Nitrogen Based (YNB), Difco™) supplemented with 0.4% glucose.

Measurement of the effect on mature (24 h-old) biofilm
Biofilms are formed in aerated microfermentors as described in "Natural conjugative plasmids induce bacterial biofilm development." by Ghigo J M, Nature, 2001 Jul. 26; 412(6845):442-5. These are formed with catheter segments fixed onto internal removable glass slides of microfermentors. Strains from the frozen stocks are cultivated in M63B1-0.4% glutamate (Glu) or YNB-0.4% Glu medium overnight. An inoculum of $10^9$ bacilli, $10^8$ cocci, or $10^7$ *Candida albicans* cells is used to inoculate microfermentors containing the catheter segments. Continuous flow of 100 mL/h of either M63B1-0.4% Glu medium (bacterial strains) or YNB-0.4% Glu (yeast) and constant aeration with sterile pressed air (0.3 bar) are used to obtain continuous flow-through culture conditions. Such a high input of fresh medium avoids significant planktonic growth. After 24 h of incubation, the segments are removed from the incubator and separated from the device.

Each segment is then carefully rinsed in 1 mL of saline. To determine the number of viable cells within the biofilms formed onto the catheter segments, the biofilms (triplicate for each strain) are resuspended in 5 ml M63B1 minimal or YNB medium by sonication and vortexing. Serial dilutions of the resulting suspensions are performed and plated onto appropriate agar plates to determine the number of viable cells [Colony Forming Unit (CFU)] after overnight incubation at 37° C. The bacteria count is expressed as a decimal logarithm (log 10).

The limit of detection in the experimental conditions is 1.6 log 10 (40 CFU) per KT segment. In parallel, segments to be tested are placed in a tube containing 1 mL of the different lock solutions: (i) ethanol at 25%, (ii) trisodium citrate at 5%, 10%, 15%, (iii) Ethanol/Citrate mixing solutions (25%-5%, 25%-10%, 25%-15%) and (iv) 0.9% sodium chloride as control. For every organism, the experiments are repeated in triplicate, and during each treatment assay segments are exposed to the different solutions for 4, 24 and 48 h at 37° C. Subsequently, the segments are removed, rinsed once with saline and the number of adherent viable microorganisms (CFU) is determined as described above.

Example II

Solutions to be tested:
Ethanol 25% (vol/vol)+trisodium citrate 5%-10% and 15%
Controls: Ethanol 25%, trisodium citrate 5%, trisodium citrate 10%, trisodium citrate 15%, saline
Material to be tested:
Segments (each 1 centimeterm long) of sterile catheters (Chronoflex™, Carbothane™, Silicone, Tecothane™ and Pellethane®).
Strains:
*Staphylococcus epidermidis* CIP 68.21
*Staphylococcus aureus* CIP 65.25 (methicillin resistant)
*Pseudomonas aeruginosa* ATCC 27853
*Klebsiella pneumoniae* LM21
*Candida albicans* SC5314

Measurement of the effect on biofilm formation

Solutions: (i) ethanol at 25%, (ii) trisodium citrate at 5%, 10%, 15%, (iii) Ethanol/Citrate mixing solutions (25%-5%, 25%-10%, 25%-15%) and (iv) 0.9% sodium chloride as control.

Catheter segments (1 cm long) are introduced into 24-well plates.

Control and lock solutions are inoculated with bacterial/fungal suspensions to yield a turbidity equivalent to that of a 0.5 McFarland standard (initial densities of $1\times10^6$ CFU/mL, 1/100 dilution) in LB broth (bacteria) or YNB-0.4% Glu (fungi).

0.5 ml of the lock solution (or control) with the inoculum are introduced into each well containing the segments. Plates are placed on a rocker at 90 rpm and incubated at 37° C. for 72 h. Every 24 h growth medium is supplemented with fresh nutrient solution to support microorganism growth in the device.

To determine the bacterial loads on each catheter segment after 72 h, the segments are transferred to wells filled with 500 µL of saline and placed back on the rocker for 1 min. to remove the residual organisms from the segment surfaces.

The segments are then placed in 0.5 mL of normal saline and sonicated for 5 min. to disrupt any biofilm. Samples from the resultant solution are plated on LB agar and incubated for 72 h. Plates are inspected every 24 h for viable colonies. The lower limit of detection is 1.6 log 10 (40 CFU). All isolates are tested in duplicate on separate days.

It will be apparent to those skilled in the art that numerous modifications and variations of the described examples and embodiments are possible in light of the above teachings of the disclosure. The disclosed examples and embodiments are presented for purposes of illustration only. Other alternate embodiments may include some or all of the features disclosed herein. Therefore, it is the intent to cover all such modifications and alternate embodiments as may come within the true scope of this invention, which is to be given the full breadth thereof. Additionally, the disclosure of a range of values is a disclosure of every numerical value within that range, including the end points.

We claim:

1. A method of treating for biofilm, comprising:
   introducing a solution consisting 4 to 10 weight/volume % ("w/v %") trisodium citrate and 25 volume/volume % ("v/v %") ethyl alcohol to a targeted environment; and,
   maintaining contact between the solution and the targeted environment to at least one of prevent biofilm generation and eradicate biofilm that has been generated at the targeted environment; and,
   wherein the targeted environment is free from trisodium citrate precipitation.

2. The method according to claim 1, wherein the maintaining contact step is capable of generating a sterile targeted environment that is blood coagulant free.

3. The method according to claim 1, wherein the solution exhibits a pH within a range from 4.0 to 8.0.

4. The method according to claim 1, wherein the targeted environment is at least a portion of a catheter system.

5. The method according to claim 4, wherein the maintaining contact step is capable of preventing thrombus formation within the catheter system.

6. The method according to claim 4, further comprising flushing the at least the portion of the catheter system before introducing the solution.

7. The method according to claim 4, further comprising applying positive pressure within the at least the portion of the catheter system during at least one of before the introducing step and after the maintaining contact step.

8. The method according to claim 1, further comprising aspiration of the solution after the maintaining contact step.

9. The method according to claim 1, further comprising at least one of:
   allowing at least a portion of the solution to enter a bloodstream of a patient after the maintaining contact step; and
   forcing at least a portion of the solution to enter the bloodstream of the patient after the maintaining contact step; and,
   wherein the entrance of the solution into the bloodstream does not pose a toxicity risk to the patient.

10. The method according to claim 1, further comprising renewing the solution after a predetermined period of time has elapsed during the maintaining contact step.

11. An aqueous catheter locking solution, consisting of:
    4 to 10 weight/volume % ("w/v %") of trisodium citrate;
    25.0 volume/volume % ("v/v %") of ethyl alcohol; and water.

12. An aqueous catheter locking solution, consisting of:
    10 weight/volume % ("w/v %") of trisodium citrate;
    25 volume/volume % ("v/v %") of ethyl alcohol; and water.

13. An aqueous catheter locking solution, consisting of:
    4 weight/volume % ("w/v %") of tri sodium citrate;
    25 volume/volume % ("v/v %") of ethyl alcohol; and water.

* * * * *